(12) United States Patent
Mylonas

(10) Patent No.: US 12,144,759 B2
(45) Date of Patent: Nov. 19, 2024

(54) POSTURAL ORTHOSIS SUPPORT APPARATUS FOR PERSONAL BODY ARMOR CARRIERS

(71) Applicant: Jim Mylonas, Stouffville (CA)

(72) Inventor: Jim Mylonas, Stouffville (CA)

( * ) Notice: Subject to any disclaimer, the term of this patent is extended or adjusted under 35 U.S.C. 154(b) by 1085 days.

(21) Appl. No.: 16/964,942

(22) PCT Filed: Jan. 29, 2019

(86) PCT No.: PCT/CA2019/050103
§ 371 (c)(1),
(2) Date: Jul. 24, 2020

(87) PCT Pub. No.: WO2019/144243
PCT Pub. Date: Aug. 1, 2019

(65) Prior Publication Data
US 2021/0038418 A1 Feb. 11, 2021

Related U.S. Application Data

(60) Provisional application No. 62/623,026, filed on Jan. 29, 2018.

(51) Int. Cl.
*A61F 5/02* (2006.01)
*F41H 1/02* (2006.01)

(52) U.S. Cl.
CPC .............. *A61F 5/024* (2013.01); *A61F 5/028* (2013.01); *F41H 1/02* (2013.01)

(58) Field of Classification Search
CPC .. F41H 5/023; F41H 1/02; A61F 5/024; A61F 5/028; A61F 5/02; A61F 5/026;
(Continued)

(56) References Cited

U.S. PATENT DOCUMENTS 3,945,376 A * 3/1976 Kuehnegger ........... A61F 5/024
602/19
5,188,585 A * 2/1993 Peters ..................... A61F 5/028
2/311

(Continued)

FOREIGN PATENT DOCUMENTS

CA    2951395 A1    1/2018

OTHER PUBLICATIONS

Danis, C. G.; Krebs, D. E.; Gill-Body, K. M.; Sahrmann, S., May 1998, "Relationship between standing posture and stability", Journal of the American Physical Therapy Association, pp. 502-517.
(Continued)

*Primary Examiner* — Ophelia A Hawthorne
(74) *Attorney, Agent, or Firm* — Phillip C. Mendes da Costa; BERESKIN & PARR LLP/S.E.N.C.R.L., s.r.l.

(57) ABSTRACT

A postural orthosis support apparatus for use with a personal body armor carrier includes a resilient semi-rigid base panel and at least one cushioning element. The base panel has a curvature for promoting a desired alignment of a spine of a user. The base panel includes a low temperature thermoplastic material, so that the curvature may be custom molded directly on the thoracic and lumbar areas on a person's back to ergonomically improve and support optimal posture. The postural orthosis support apparatus is configured to be secured to a personal body armor carrier interior of a ballistic panel.

19 Claims, 15 Drawing Sheets

(58) Field of Classification Search
CPC .... A61F 2250/001; A61F 5/0102; A61F 5/03; A61F 5/3738; A61F 9/029; A61F 5/0127; A61F 5/013; A61F 5/0193; A61F 5/055; A61F 5/34; A61F 2002/5018; A61F 2002/5026; A61F 2002/5001; A61F 2002/5083; A61F 2002/587; A61F 5/01; A61F 5/022; A61B 5/681; A61B 5/02427; A61B 5/02416; A61B 5/1123; A61B 5/02433; A61B 5/02438; A61B 5/1118; A61B 5/4812; A61B 5/0002; A61B 5/0205; A61B 5/11; A61B 5/6843; A61B 5/6844; A61B 17/04; B60N 2205/35; B60N 2/3013; B60N 2/36; B60N 2/366; B60N 2/682; B60N 2/686; B60N 3/02; A61G 1/044; A61G 7/0504; A62B 1/02; B65D 88/14; A61H 1/02; A61H 1/0218; A45F 3/08

See application file for complete search history.

(56) References Cited

U.S. PATENT DOCUMENTS

| | | | | |
|---|---|---|---|---|
| 5,407,248 | A * | 4/1995 | Jay | A61G 5/12 297/284.3 |
| 10,274,289 | B1 * | 4/2019 | Barnhart, II | F41H 1/02 |
| 2004/0147861 | A1 * | 7/2004 | Kozersky | A61F 5/022 602/5 |
| 2004/0220502 | A1 * | 11/2004 | Arden | A61F 5/0109 602/19 |
| 2006/0144885 | A1 * | 7/2006 | Smeuninx | A45F 3/047 224/644 |
| 2008/0113143 | A1 * | 5/2008 | Taylor | B32B 5/32 428/47 |
| 2010/0152636 | A1 | 6/2010 | Parks et al. | |
| 2010/0318010 | A1 * | 12/2010 | Sandifer | A61F 5/026 602/19 |
| 2013/0019881 | A1 * | 1/2013 | Bhat | A61F 5/01 5/655.5 |
| 2013/0221051 | A1 * | 8/2013 | Hairston | A45C 13/04 156/305 |
| 2015/0189974 | A1 * | 7/2015 | Bercaw | A45F 3/04 224/633 |
| 2015/0208791 | A1 * | 7/2015 | Klein | A45F 3/08 224/633 |
| 2016/0038330 | A1 | 2/2016 | Kim | |
| 2018/0200098 | A1 * | 7/2018 | Swanson | A61F 5/028 |

OTHER PUBLICATIONS

Danish Institute for Health Technology Assessment (HTA): "Low-Back Pain: Frequency, Management and Prevention from an HTA Perspective", at least as early as Jan. 1999, copy attached (retrieved from https://chiro.org/Low_Back_Pain/Low_Back_Pain_Frequency_Management.html).

Statistics Canada, National Population Health Survey: General Information and Products and Services, at least as early as 1999, Public use database.

Alberta Human Resources and Employment: "Occupational injuries and diseases in Alberta 2001 Summary", Jul. 2002, Table 4.3.

Konitzer L.N. et al. "Association between back, neck, and upper extremity musculoskeletal pain and the individual body armor", Apr.-Jun. 2008; Journal of Hand Therapy, 21(2):143-8.

Keller TS, Colloca CJ, 25 Harrison DE, Harrison DD, Janik TJ : "Influence of spine morphology on intervertebral disc loads and stresses in asymptomatic adults: implications for the ideal spine", Spine J. May-Jun. 2005; 5(3):297-309.

International Search Report and Written Opinion (Corrected Versions), received in connection to the corresponding international patent application No. PCT/CA2019/050103, mailing date of Apr. 9, 2019.

* cited by examiner

POSTURAL ORTHOSIS SUPPORT APPARATUS FOR PERSONAL BODY ARMOR CARRIERS

CROSS REFERENCE TO RELATED APPLICATIONS

This application claims benefit under 35 U.S.C. 371 based on co-pending International Patent Application No. PCT/CA2019/050103, filed on Jan. 29, 2019, which itself claims priority from U.S. Provisional Patent Application No. 62/623,026, filed on Jan. 29, 2018, the contents of which are incorporated herein by reference in their entirety.

FIELD

This disclosure relates generally to postural orthosis for personal body armor carriers, and more specifically to an apparatus for providing corrective postural back support or orthosis to a user while wearing soft body armor or carrying portable equipment on the torso.

INTRODUCTION

An ideal posture, also referred to as a neutral posture, may result from a proper alignment of the spine. A neutral posture may provide a wide variety of benefits. For example, a lower amount of energy may be required to maintain any desired position and movement may facilitated within preferred and/or optimal bio-kinematic ranges. Achieving and maintaining a neutral or ideal posture may also reduce the stress placed on the body's tissues. See, for example, Danis, C. G.; Krebs, D. E.; Gill-Body, K. M.; Sahrmann, S. (1998), *Relationship between standing posture and stability*, Journal of the American Physical Therapy Association, pp. 502-517. An ideal or neutral posture may also improve breathing, oxygenation, and/or circulation of bodily fluids such as lymph, cerebral spinal fluid, and blood.

Postural alterations or modifications that deviate from an ideal or neutral posture are known to be associated with numerous afflictions such as: general pain syndromes (for example, low back pain, neck pain, headaches); problems with specific joints (for example the hip and knee); problems with specific spinal regions (for example, loss of normal low back curve, and thoracic hyperkyphosis); and various organ ailments (for example, gastric herniation, and impaired respiratory function).

Low-back pain may be defined as tiredness, discomfort, or pain in the low back region, with or without radiating symptoms to the leg or legs (See e.g. Danish Institute for Health Technology Assessment (HTA), 1999). Low-back pain is a condition that usually begins at working age. It may be characterized as a widespread condition. For example, in 1999 in Alberta, Canada, 17 percent of persons between the ages of 20 and 39, and 20 percent of persons between the ages of 40 and 49, reported having low-back pain (Statistics Canada, National Population Health Survey 1999, Public use database). In 2001 in Alberta, out of a total of 37,927 work loss claims, 26.8 percent were associated with low-back pain (Alberta Human Resources and Employment, Occupational injuries and diseases in Alberta, 2001 Summary, July 2002, Table 4.3).

Low-back pain may also be characterized as a costly condition, in large part because it is associated with time off from work. In a U.S. based survey by Andersson et al., (1991) the overall annual cost per case varied from $3,000 to $6,600. Roughly one-third of these costs were incurred for medical expenses, and two-thirds were due to disability. In a widely quoted U.S. study conducted for the American Academy of Orthopedic Surgeons in 1984, Grazier et al. (1984) stated that the annual costs of low-back pain were over $16 billion. The estimates from these studies are indicative of the magnitude of the problem.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

The carrying of portable equipment on the back or torso may cause, or exacerbate, a person to deviate from an ideal or neutral posture. For example, military and law enforcement personnel often wear personal body armor. A cross-sectional randomized survey of 863 U.S. Soldiers in Iraq revealed a substantial increase in the incidence of back, neck, and upper extremity pain during deployment, and approximately twice as many soldiers attributed their musculoskeletal pain to wearing body armor than to job tasks and physical training (Konitzer L N, et al. *Association between back, neck, and upper extremity musculoskeletal pain and the individual body armor*, Journal of Hand Therapy. 2008 April-June). Due to the rigid nature and necessary weight of the armor needed to provide the desired protection, users of body armor often complain about lack of comfort and various ailments, which may be linked to deviating from an ideal or neutral posture. In particular, modern body armor does not typically contain any thoracic or lumbar support.

A variety of non-custom load distribution devices for use with load bearing equipment worn on the torso such as body armor are known. For example, some devices serve to distribute the weight of the portable equipment to the hips. However, these devices typically do not correct posture or provide support to the spine.

Custom molded splints for the torso to correct postural dysfunctions are known. These medical devices typically surround and immobilize the torso and require a means of being attached to the torso via straps, girdles, etc. and are not integrated into equipment worn on the torso. Also, such splinting devices tend to significantly restrict a user's range of motion throughout the thoracic and lumbar spine.

The apparatus and methods disclosed herein may provide a custom molded, corrective and removable low back support insert that can be used interchangeably between various different makes and types of body armor carriers by the wearer. The use of such an orthotic insert with a body armor carrier may have one or more advantages. For example, it may mitigate low back stress, correct postural dysfunctions, and/or improve and preferably optimize postural support. Additionally, or alternatively, it may not significantly decrease the range of motion of a user wearing a body armor carrier with such an insert.

Use of the apparatus and methods disclosed herein may also may improve the comfort of a user while wearing body armor or carrying portable equipment on the back or torso. Wearing body armor or such portable equipment may cause the user to deviate from an ideal or neutral posture. For example, personal body armor often includes storage pockets for ancillary equipment, such as ammunition and the like, on the front for ease of access. The rigidity of the armor (e.g.

of ballistic panels), the overall weight of the armor and any ancillary equipment, an unequal weight distribution, and prolonged exposure are various factors that may contribute to a user deviating from the ideal or neutral posture. The apparatus disclosed herein may also help support proper lumbar curvature during sitting in vehicles for prolonged periods.

In one or more preferred embodiments, the postural support device may be custom molded to a particular user. For example, a curvature in a thermoplastic base panel may be custom molded directly on the thoracic and lumbar areas on the back of the body to ergonomically improve and support optimal posture in the wearer of the body armor according to their needs by conforming to the optimal human thoracic and lumbar curve or to correct a specific postural dysfunction. Optionally, the spine of a user may be positioned into a neutral or optimal position prior to the custom molding process.

In accordance with a first broad aspect, there is provided a postural orthosis support apparatus for use with a personal body armor carrier, the orthosis support apparatus comprising: a resilient semi-rigid base panel comprising a low temperature thermoplastic, the base panel having an upper end, a thoracic portion, a lumbar portion, a lower end, a front face, and a rear face, the base panel having a curvature for promoting a desired alignment of a spine of a user; and at least one base cushioning element having a front face, a rear face secured to the front face of the base panel, a thoracic portion, and a lumbar portion; wherein the base panel is configured to be secured to the personal body armor carrier interior of a ballistic panel.

In some embodiments, the semi-rigid base panel may further comprise at least one of an aramid, a para-aramid, and an ultra-high-molecular-weight polyethylene.

In some embodiments, the curvature may be custom-formed to the spine of a specific user.

In some embodiments, the curvature may be formed by heating the base panel above a softening temperature, placing the heated base panel against the specific user's back to form the curvature, and allowing the base panel to cool below the softening temperature while maintaining the curvature.

In some embodiments, the postural orthosis support apparatus may further comprise a supplementary cushioning element configured to be releasably secured to the front face of the lumbar portion of the base cushioning element.

In some embodiments, a rear face of the supplementary cushioning element may be configured to be releasably secured to the front face of the lumbar portion of the base cushioning element by complementary hook and loop fastening elements.

In some embodiments, the base panel may further comprise an engagement flange extending rearwardly and upwardly from the base panel proximate the lower end of the base panel, the engagement flange and the rear face of the base panel defining an upwardly facing channel for engaging a lower edge of the ballistic panel.

In some embodiments, the engagement flange may be formed by heating the base panel above a softening temperature, folding a lower portion of the base panel back towards itself to form the engagement flange and the channel, and allowing the base panel to cool below the softening temperature.

In some embodiments, at least one interior surface of the upwardly facing channel may have a textured surface for inhibiting relative movement between the base panel and the ballistic panel when the lower edge of the base panel is engaged by the upwardly facing channel.

In some embodiments, the rear face of the base panel may be releasably secured to at least one of the ballistic panel and the personal body armor carrier by complementary hook and loop fastening elements.

In some embodiments, the rear face of the at least one base cushioning element may be releasably secured to the front face of the base panel by complementary hook and loop fastening elements.

In some embodiments, the at least one base cushioning element may cover substantially all of the front face of the base panel.

In some embodiments, the rear face of the at least one base cushioning element may comprise a securement layer that covers substantially all of the front face of the base panel, wherein a plurality of cushioning segments extended forwardly from the securement layer, and wherein at least one ventilation channel is defined by sides of adjacent cushioning segments and the securement layer.

In some embodiments, one of the at least one base cushioning element may have a first thickness, and another of the at least one base cushioning element may have a second thickness that is less than the first thickness.

In some embodiments, one of the plurality of cushioning segments may have a first thickness, and another of the plurality of cushioning segments may have a second thickness that is less than the first thickness.

In some embodiments, one of the at least one base cushioning element may have a first density, and another of the at least one base cushioning element may have a second density that is less than the first density.

In some embodiments, one of the plurality of cushioning segments may have a first density, and another of the plurality of cushioning segments may have a second density that is less than the first density.

It will be appreciated by a person skilled in the art that a method or apparatus disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

While the apparatus and methods disclosed herein are described specifically in relation to and in use with a personal body armor carrier, it will be appreciated that the apparatus and methods may alternatively be used with other types of portable equipment worn on the torso including: backpacks, fire resistant equipment, fire resistant clothing, respirator systems, gas tanks, and the like.

Figure 1:
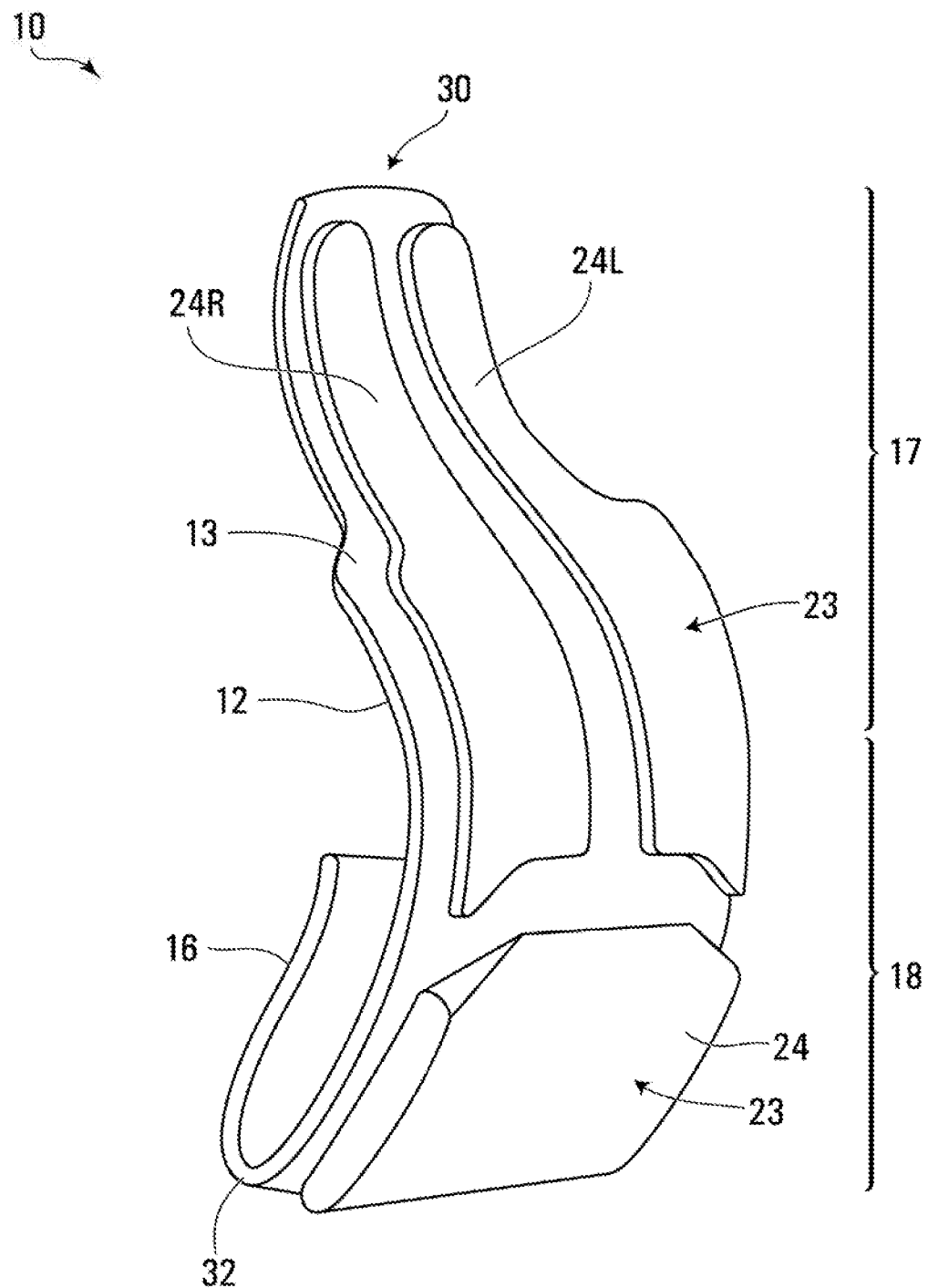
FIG. 1 is a perspective view of a postural orthosis support apparatus for use with a personal body armor carrier, in accordance with one embodiment.
Figure 2:
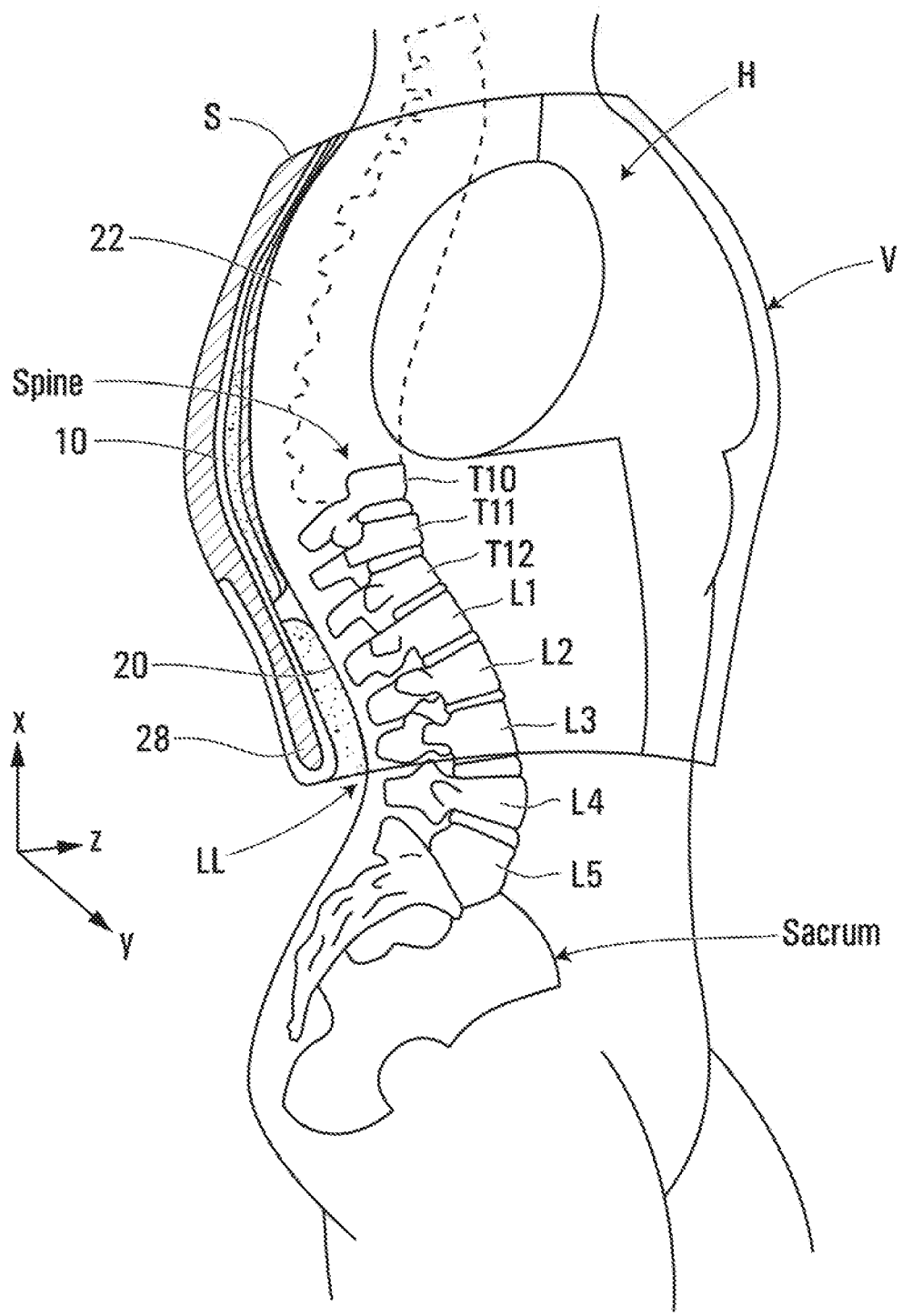
FIG. 2 is a schematic section view of the postural orthosis support apparatus of FIG. 1 in use by a user wearing a personal body armor carrier.

FIGS. 1 and 2 illustrate an embodiment of a postural orthosis support apparatus, referred to generally as 10. Postural orthosis support apparatus 10 includes a base panel 12 that has an upper end 30, a thoracic portion 17, a lumbar portion 18, a lower end 32, a front face 13, and a rear face 14. Postural orthosis support apparatus 10 also includes a number of cushioning elements 24 secured to the front face 13 of the base panel 12.

In the illustrated example, base panel 12 has a longitudinal curvature between the upper end 30 and the lower end 32. Preferably, this curvature has a shape of a preferred lumbar lordosis and thoracic kyphosis.

For example, FIG. 2 illustrates a schematic example of a human being H wearing a ballistic body armor carrier or vest V. The human being is standing with his/her spine in a preferred form of lumbar lordosis LL with vertebrae T9-T12 and L1-Sacrum in a preferred position. Such a position places the spine in an optimal or preferred shape, with the postural orthosis support apparatus 10 between the person's back 22 and back panel of a ballistic panel S carried by the body armor vest V.

Postural orthosis support apparatus 10 also includes one or more cushioning elements secured to the front face 13 of base panel 12. Cushioning elements secured to the front face may be characterized as 'base' cushioning elements. For example, base cushioning elements may be secured directly to the base panel 12 using an adhesive. Alternatively, base cushioning elements may be releasably secured to the base panel 12 using a mechanical fastener, such as Velcro® or a similar hook and loop fastener (e.g. with one or more 'hook' elements secured to the front face of base panel 12 and one or more 'loop' elements secured to the rear face of a cushioning element). Additionally, or alternatively, a base cushioning element may be retained in position against base panel 12 using a natural or synthetic material covering 26 (e.g. as in the example embodiment illustrated in FIG. 3). For example, material cover 26 may be made from a nylon, polyurethane, neoprene, or other synthetic material. It will be appreciated that for any references herein to releasable securement using 'hook' and 'loop' elements, the 'hook' and 'loop' elements may reversed (e.g. if 'hook' elements are illustrated on surface A and 'loop' elements are illustrated on surface B, in alternative embodiments the 'loop' elements may be provided on surface A and the 'hook' elements may be provided on surface B).

Base cushioning elements 24 are preferably provided at both a thoracic portion of base panel 12 and a lumbar portion of base panel 12. In the example illustrated in FIG. 1, Postural orthosis support apparatus 10 includes two thoracic cushioning elements 24R, 24L provided on the thoracic portion 17 of base panel 12, and a single lumbar cushioning element 24 provided on the lumbar portion 18 of base panel 12. Optionally, the base cushioning elements of apparatus 10 may include one or multiple pieces covering a majority, most, or substantially all of the front (anterior) surface of base panel 12.

In the example illustrated in FIG. 1, the front faces 23 of base cushioning elements 24 may be characterized as collectively defining a support face 20 that is configured to be placed against a person's back 22. It will be appreciated that a user may, and will likely, wear clothing (e.g. a shirt) on their torso when also wearing a personal body armor carrier. Thus, references to being worn on or engaging a person's back should not be construed as being limited to requiring contact with the person's skin.

Cushioning elements 24 may be made from any suitable resilient material, such as a polyurethane foam. Cushioning elements 24 may be constructed of a substantially uniform material, of a material or composite of varying densities and/or layers. For example, a cushioning element 24 may include two or more layers of different material. In the embodiment of a postural orthosis support apparatus illustrated in FIG. 3, the cushioning element 24 provided on the thoracic portion 17 of base panel 12 includes two layers 36 and 38. Layers 36 and 38 may each be constructed from a polyurethane foam or a similar material having different resiliencies or densities (e.g. 'harder' or 'softer') from each other or from a 'standard' foam material. In this way, further custom fitting may be provided for comfort and/or therapeutic reasons.

Figure 3:
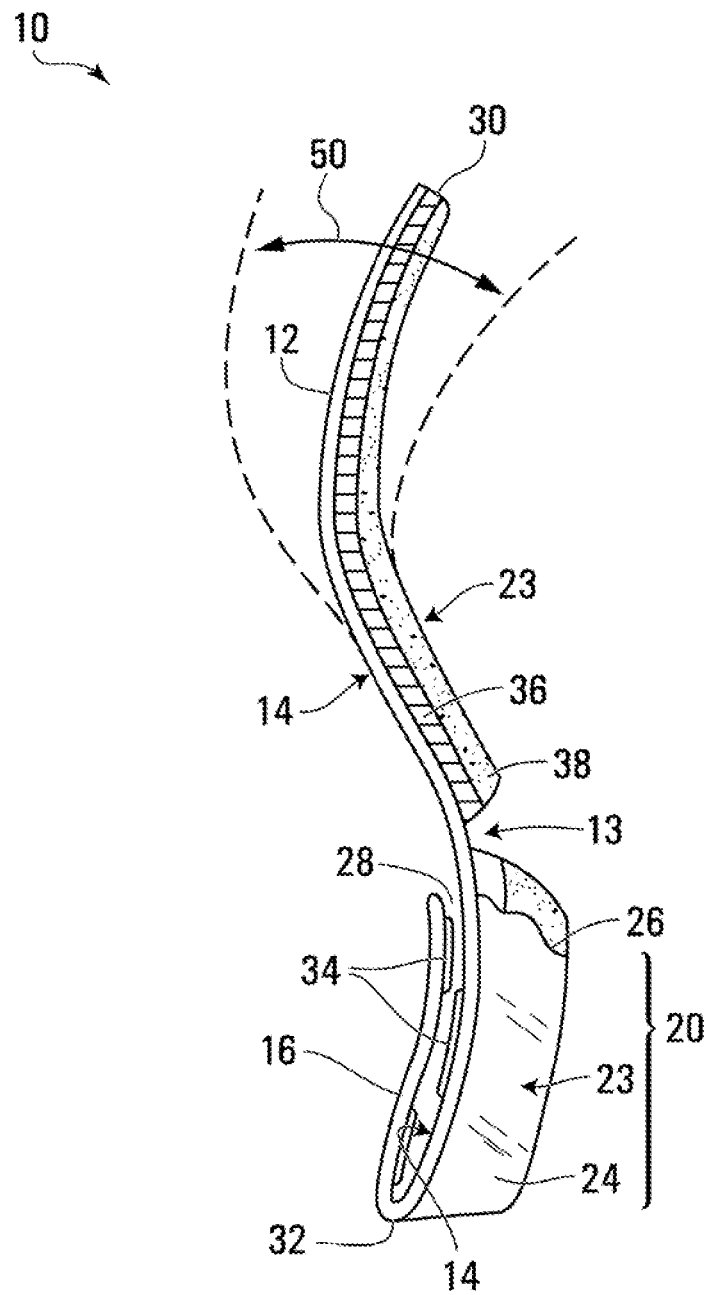
FIG. 3 is a side partial section view of a postural orthosis support apparatus for use with a personal body armor carrier, in accordance with another embodiment.

Base panel 12 is preferably semi-rigid and resiliently flexible, such that panel 12 has sufficient rigidity to retain itself in a self-supporting curvilinear shape (e.g. when cooled down after custom molding), but also exhibits sufficient flexibility to be deformed to flex forward or extend back along a longitudinal (anterior-posterior) axis of the thoracic kyphosis and lumbar lordosis (e.g. in a direction 50 as shown in FIG. 3) while being worn between a user's back and a ballistic panel of a body armor carrier. For example, base panel 12 may be sufficiently flexible so that it may be deformed by manually applied forces (e.g. a typical adult grasping a lower portion of the base panel with one hand and grasping an upper end of the base panel with their other hand would be able to bend or deflect the upper end relative to the lower portion without significant effort). It will be appreciated that the rigidity and/or resilience of base panel 12 may be a function of the material from which panel 12 is constructed and/or the thickness of the panel 12. For example, base panel 12 may be made from FiberForm® Stiff or FiberForm® Soft splinting material, as available from Chesapeake Medical Products, Inc. of Baltimore, Md., U.S.A., and have a thickness of about one eighth of an inch (⅛").

Base panel 12 may be constructed from a single material or may be a composite construction of various materials including, but not limited to: an aramid, a para-aramid such as Kevlar™, an ultra-high-molecular-weight polyethylene, a low temperature thermoplastic, Acrylonitrile butadiene styrene (ABS), a polycarbonate such as Lexan™ or Makrolon™, a laminated polycarbonate, heat stabilized nylon, carbon fibre, or other lightweight and impact resistant materials. In one or more preferred embodiments, base panel 12 may be constructed from FiberForm® Stiff or FiberForm® Soft splinting material. Preferably, base panel 12 is constructed from a relatively lightweight material, to reduce any increased loading on a user due to the weight of the apparatus 10 (i.e. in addition to the weight of a personal body armor carrier, ballistic panels, etc.).

As illustrated in FIG. 2, postural orthosis support apparatus 10 may be worn between a user's back (i.e. against the rear or posterior side of the torso) and a personal body armor carrier. Preferably, postural orthosis support apparatus 10 is configured to be secured to a personal body armor carrier interior of a ballistic panel (i.e. positioned between a ballistic panel and a user's back). In the illustrated example, postural orthosis support apparatus 10 is positioned between the person's back 22 and a back ballistic panel S of the body armor carrier V.

With reference to the example illustrated in FIG. 3, postural orthosis support apparatus 10 preferably has a height H between upper end 30 and the lower end 32 that is anywhere from e.g. the T4 to the L3/4 vertebrae, or the T4 to the L4/5 vertebrae. The height H may depend on where a lower edge of the rear ballistic panel of a personal body armor carrier (or ballistic vest) sits relative to a user's spine when the carrier is being worn by the user. Postural orthosis support apparatus 10 may have any suitable width W between the sides of base panel 12, e.g. depending on the width of a user's torso, or on the width of a rear ballistic panel of the personal body armor carrier. For example, apparatus 10 may have a width W of between about 6 inches to about 9 inches. It will be appreciated that the size and configuration of postural orthosis support apparatus 10 may be dependent on the size of the armor carrier, and/or on the size of the person who will be wearing the armor carrier.

In the embodiment of a postural orthosis support apparatus 10 illustrated in FIGS. 1 and 2, an engagement flange 16 extends rearwardly and upwardly from base panel 12 proximate the lower end 32 of base panel 12. Engagement flange 16 and the rear face 14 of base panel 12 define an upwardly facing channel 28 for engaging a lower edge of a ballistic panel. Advantageously, positioning channel 28 around a lower edge of a ballistic panel may inhibit or prevent relative movement of the postural orthosis support apparatus 10 relative the ballistic panel and/or relative to the personal body armor carrier in which the ballistic panel is retained. Put another way, the engagement of channel 28 with a ballistic panel may inhibit or prevent any undue shifting or displacement of postural orthosis support apparatus 10 without the use of any special or additional fasteners.

For example, some personal body armor carriers have a rear cavity or pocket in which a hard or soft ballistic panel may be removably placed. For such body armor carriers, a user may access the rear cavity or pocket and slide postural orthosis support apparatus 10 into a position between the ballistic panel and an interior of the rear pocket of the personal body armor carrier with a lower edge of the ballistic panel positioned in channel 28. Thus, channel 28 may allow the apparatus 10 to be placed and retained in an upright and secure position inside a rear compartment of an armor carrier without the need of fasteners.

Figure 5:
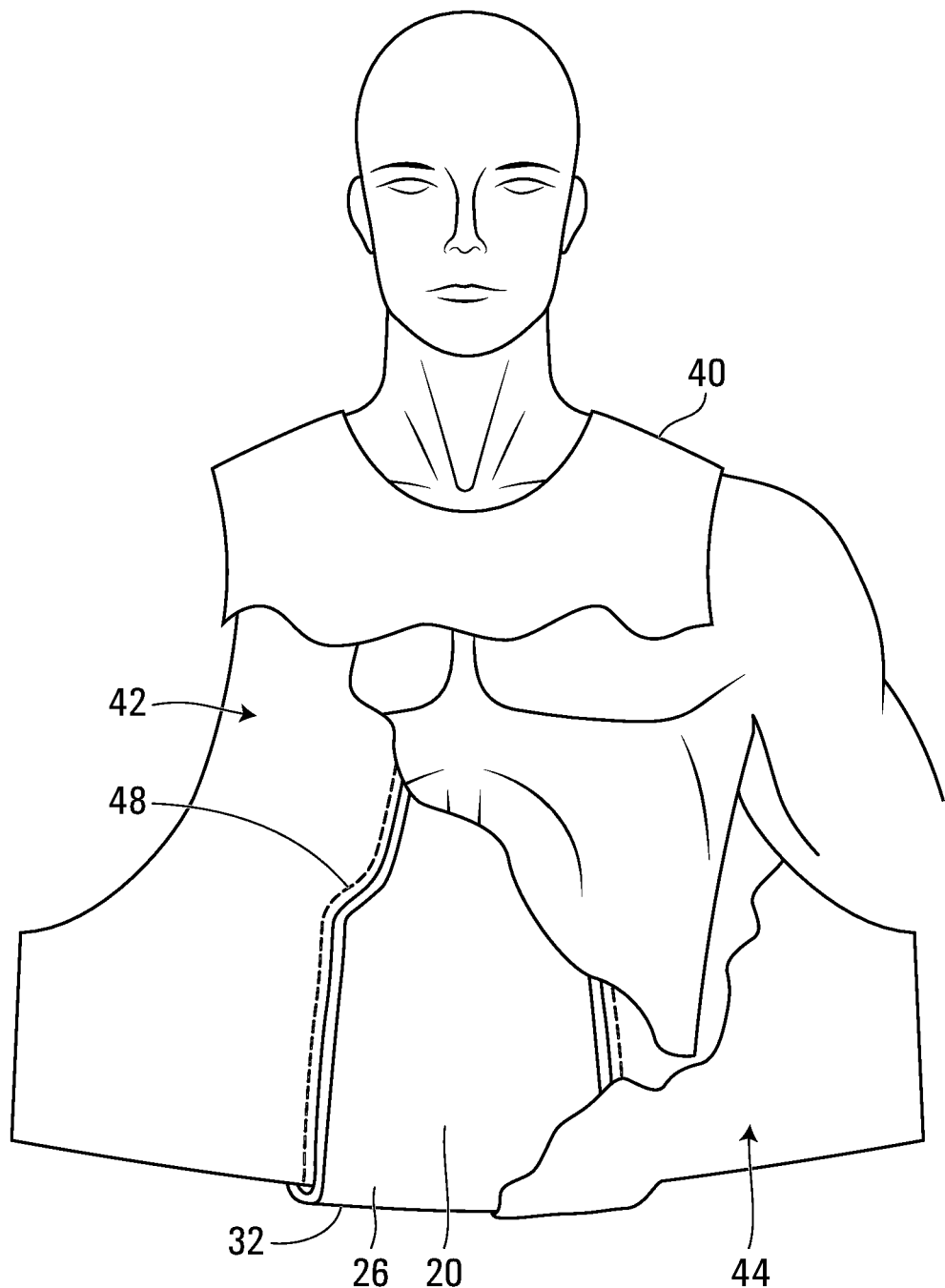
FIG. 5 is a schematic front partial section view of a postural orthosis support apparatus in use by a user wearing a personal body armor carrier.
Figure 6:
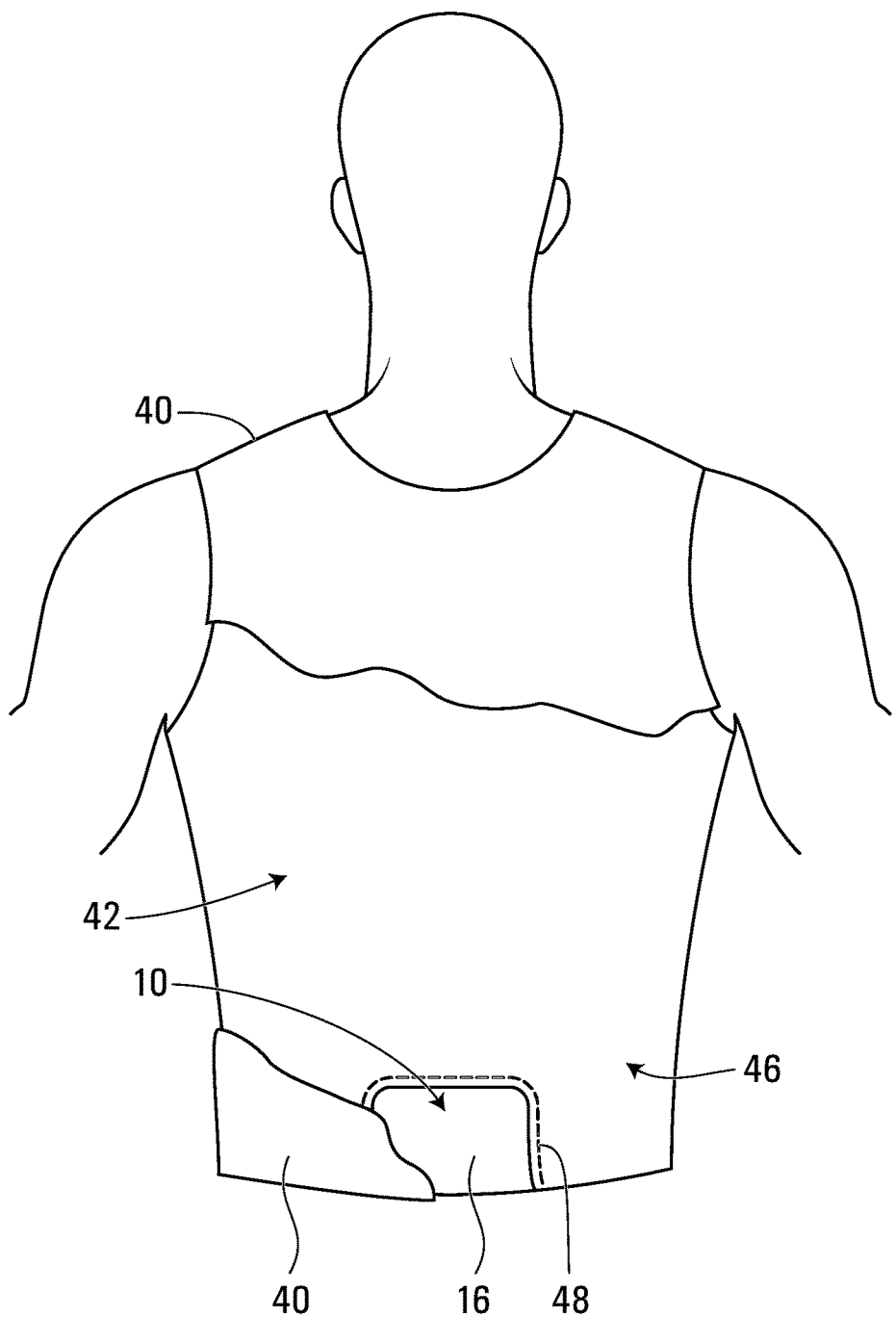
FIG. 6 is a schematic rear partial section view of the postural orthosis support apparatus of FIG. 5.

Optionally, postural orthosis support apparatus 10 may be secured within a personal body armor carrier. For example, postural orthosis support apparatus 10 may be fixed within a personal body armor carrier by being sewn, or otherwise retained in position within the fabric of an armor carrier 40. As illustrated in FIGS. 5 and 6, a postural orthosis support apparatus 10 may be secured using stitching 48 around its perimeter to integrate it with a back panel 42 of a soft body armor carrier 40. As shown schematically in FIG. 5, base panel 12 is positioned interior of a rear ballistic panel, with support face 20 facing a user's back. As shown schematically in FIG. 6, engagement flange 16 is positioned exterior of the rear ballistic panel, with a lower edge of the ballistic panel positioned within channel 28. In the illustrated example, stitching 48 is provided around substantially all of a perimeter of postural orthosis support apparatus 10, although it will be appreciated that stitching 48 may only be provided about a portion of the perimeter (e.g. above a portion of the upper end 30 of base panel 12, and portions on either side of the lower end 32 of base panel 12) in one or more alternative embodiments.

Figure 4:
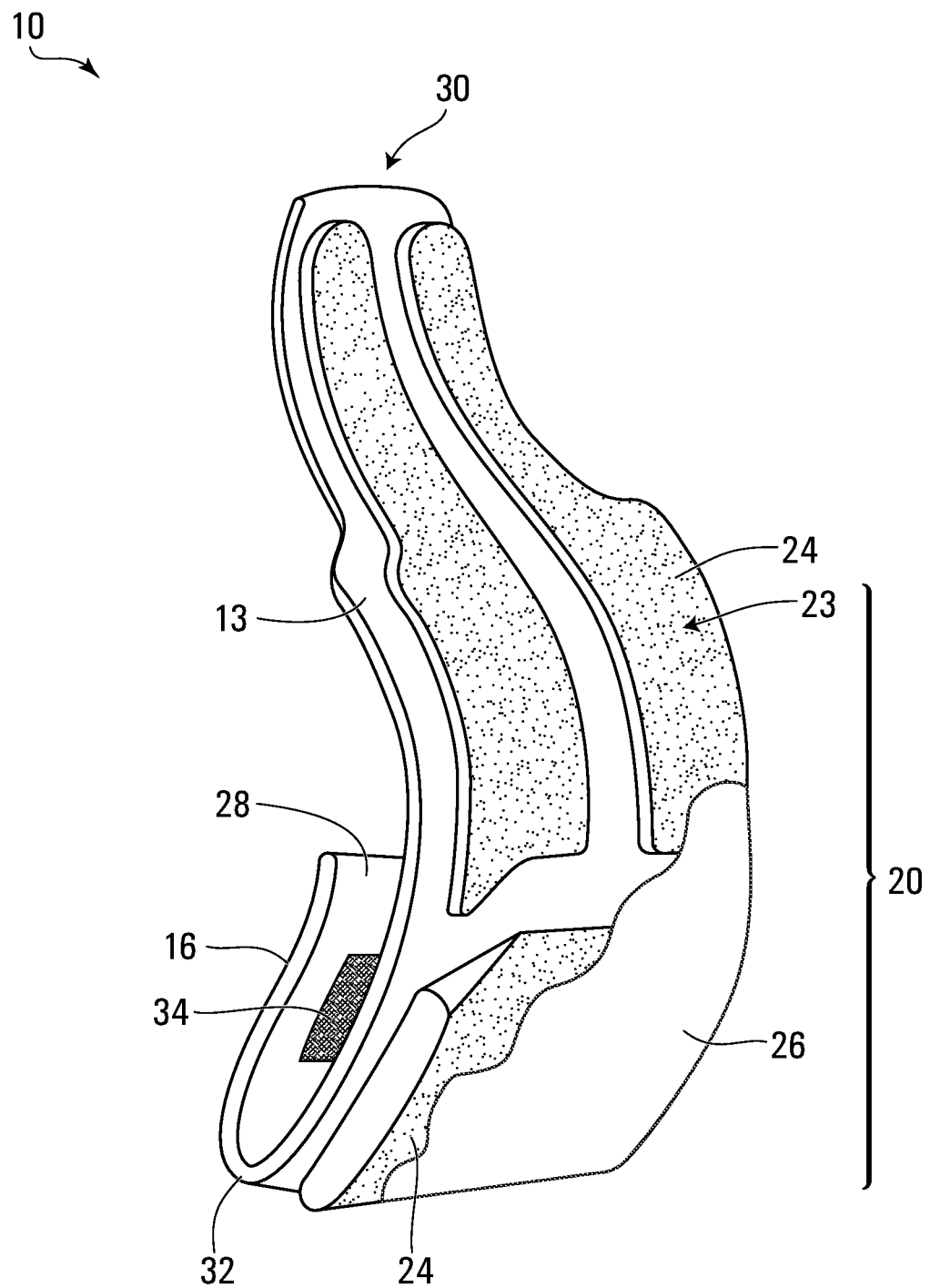
FIG. 4 is a perspective partial section view of a postural orthosis support apparatus for use with a personal body armor carrier, in accordance with another embodiment.

Optionally, at least one interior surface of the upwardly facing channel 28 may include a textured surface for inhibiting relative movement between the base panel and a ballistic panel engaged by the channel 28. In the example illustrated in FIG. 3, non-slip gripping areas 34 are shown on the interior surfaces of both base panel 12 and engagement flange 16 portions that define channel 28. In the example illustrated in FIG. 4, a non-slip gripping area 34 is shown on the interior surfaces of engagement flange 16. For example, the gripping areas 34 may be provided by a rubberized material having a textured surface that has been secured to inner surfaces of channel 28 using an adhesive.

Figure 16:
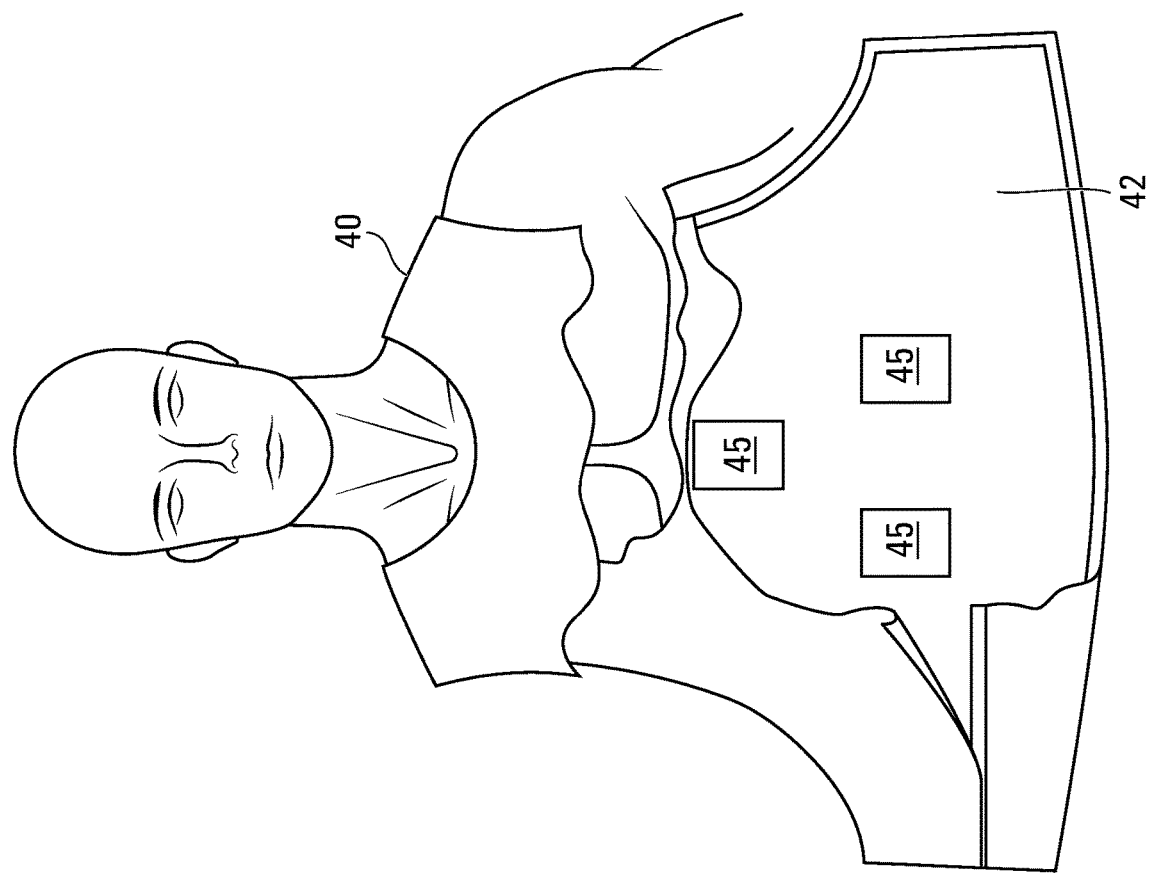
FIG. 16 is a schematic front partial section view of a user wearing a personal body armor carrier.
Figure 15:
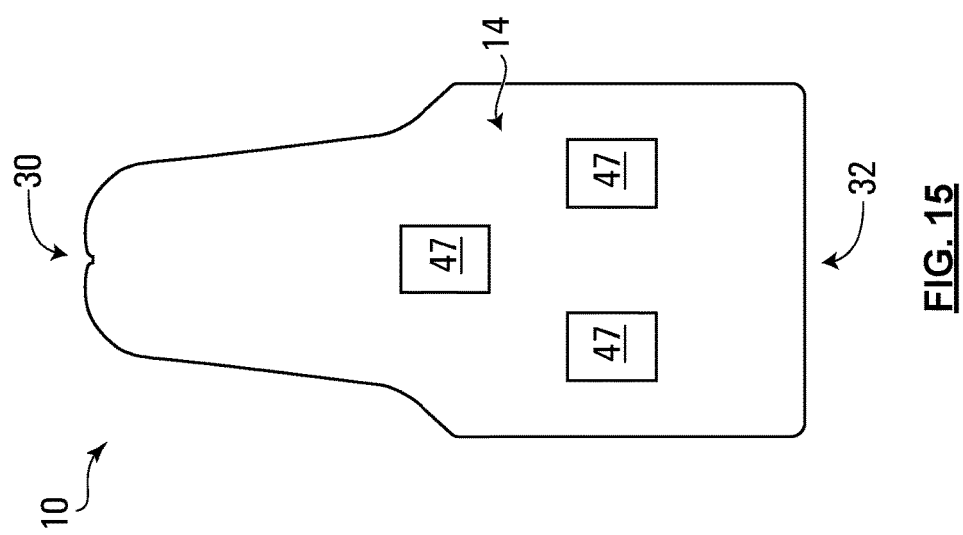
FIG. 15 is a schematic rear view of a the postural orthosis support apparatus in accordance with another embodiment.

In one or more alternative embodiments, postural orthosis support apparatus 10 may not be provided with an engagement flange or an upwardly facing channel for receiving a ballistic panel. In such embodiments, a rear face 14 of base panel 12 may be releasably securable to an interior face 42 of a personal body armor carrier (or an interior face of a ballistic panel installed within a body armor carrier) using a mechanical fastener, such as hook and loop fasteners. In the example illustrated in FIGS. 15 and 16, a number of 'hook' elements 47 are secured to the rear face 14 of base panel 12 (e.g. using an adhesive) and one or more 'loop' elements 45 are provided on an interior face of a body armor carrier.

Figure 9:
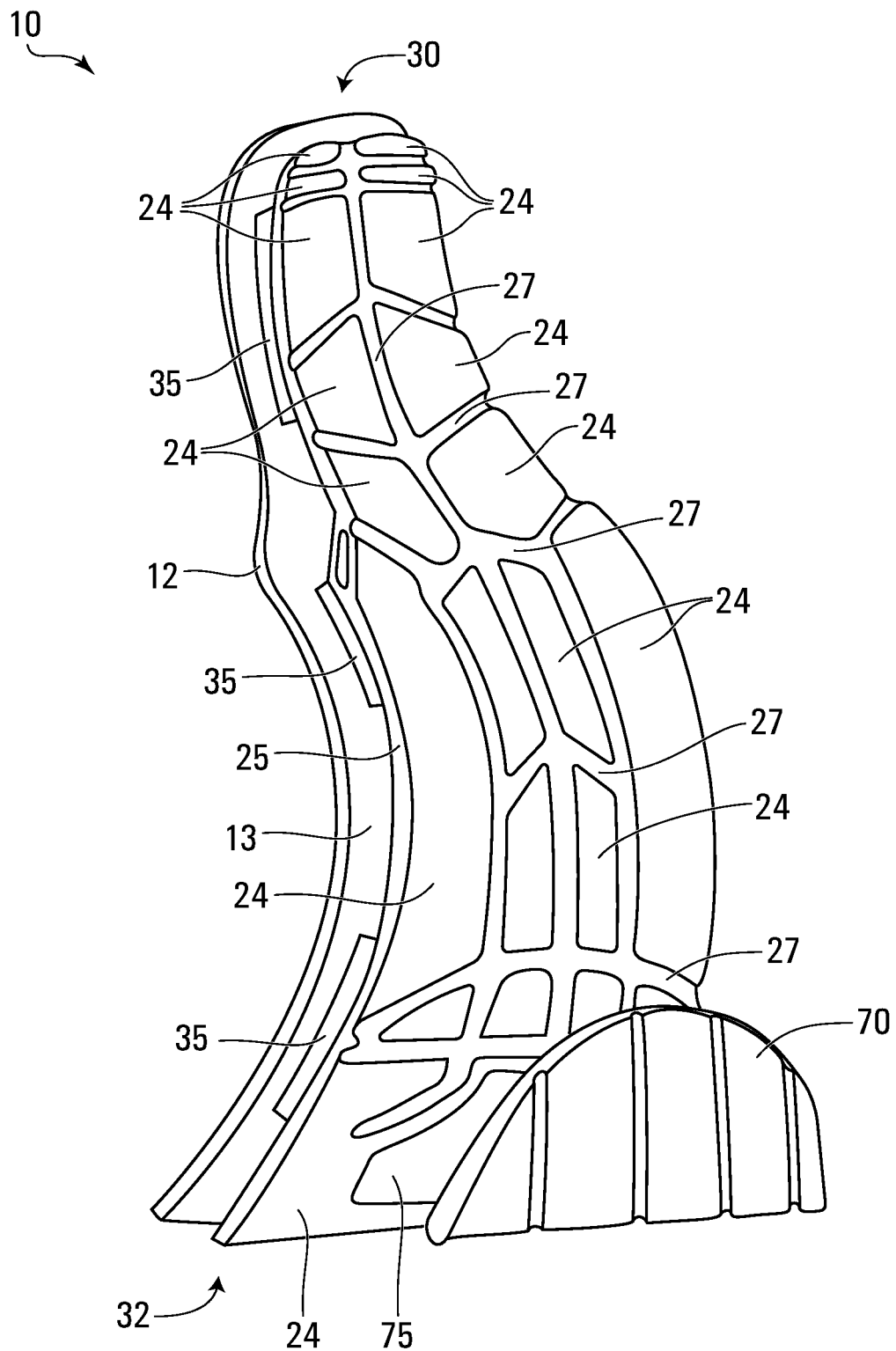
FIG. 9 is an exploded perspective view of a postural orthosis support apparatus for use with a personal body armor carrier, in accordance with another embodiment.
Figure 10:
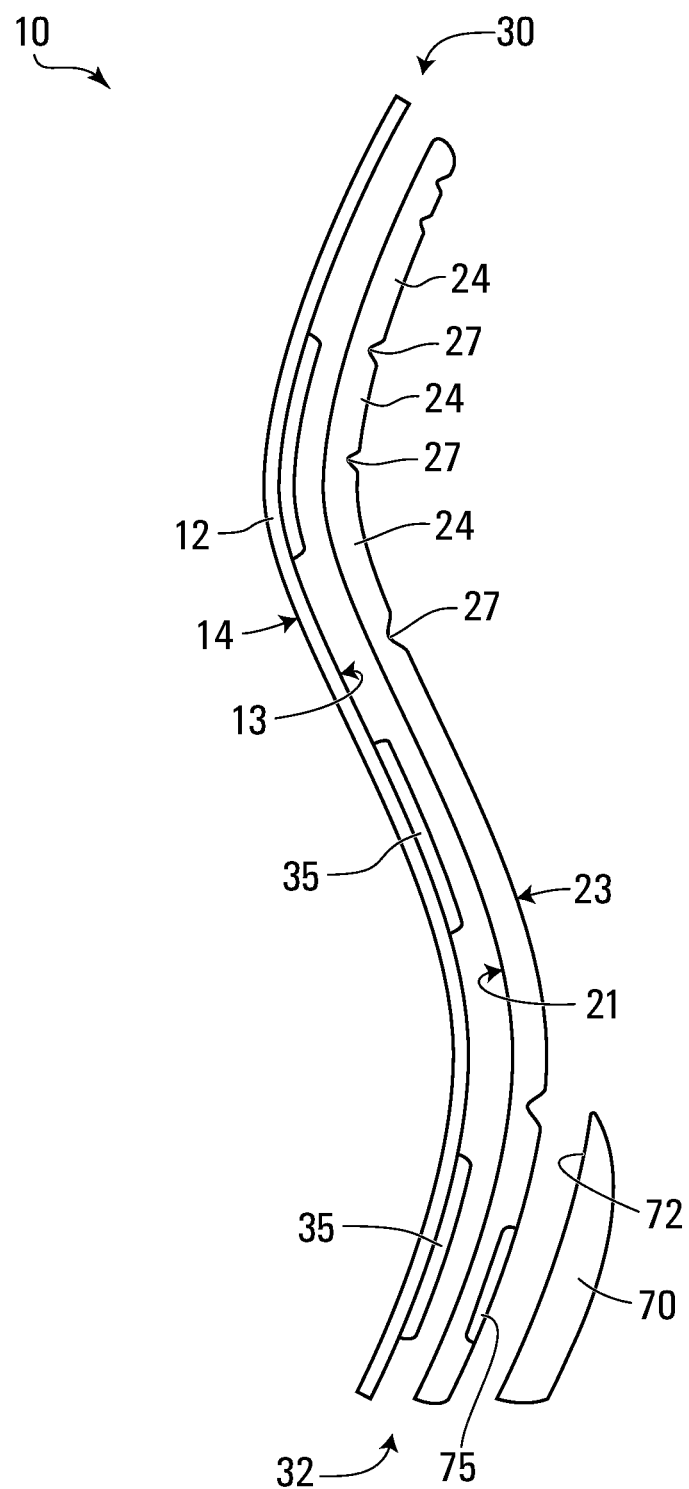
FIG. 10 is an exploded side view of the postural orthosis support apparatus of FIG. 9.
Figure 11:
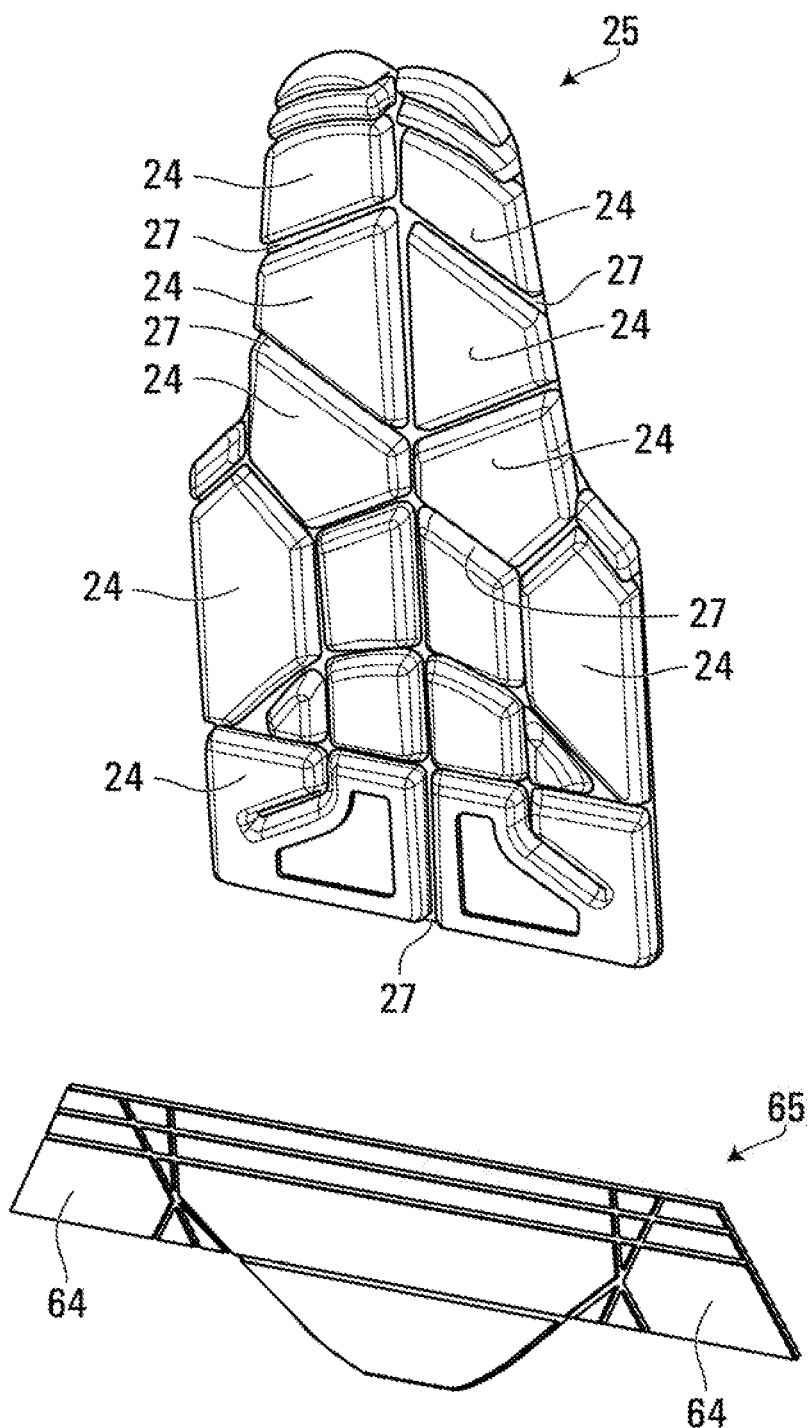
FIG. 11 is a perspective view of a base cushioning element according to one embodiment, and a variable cushioning element.
Figure 12:
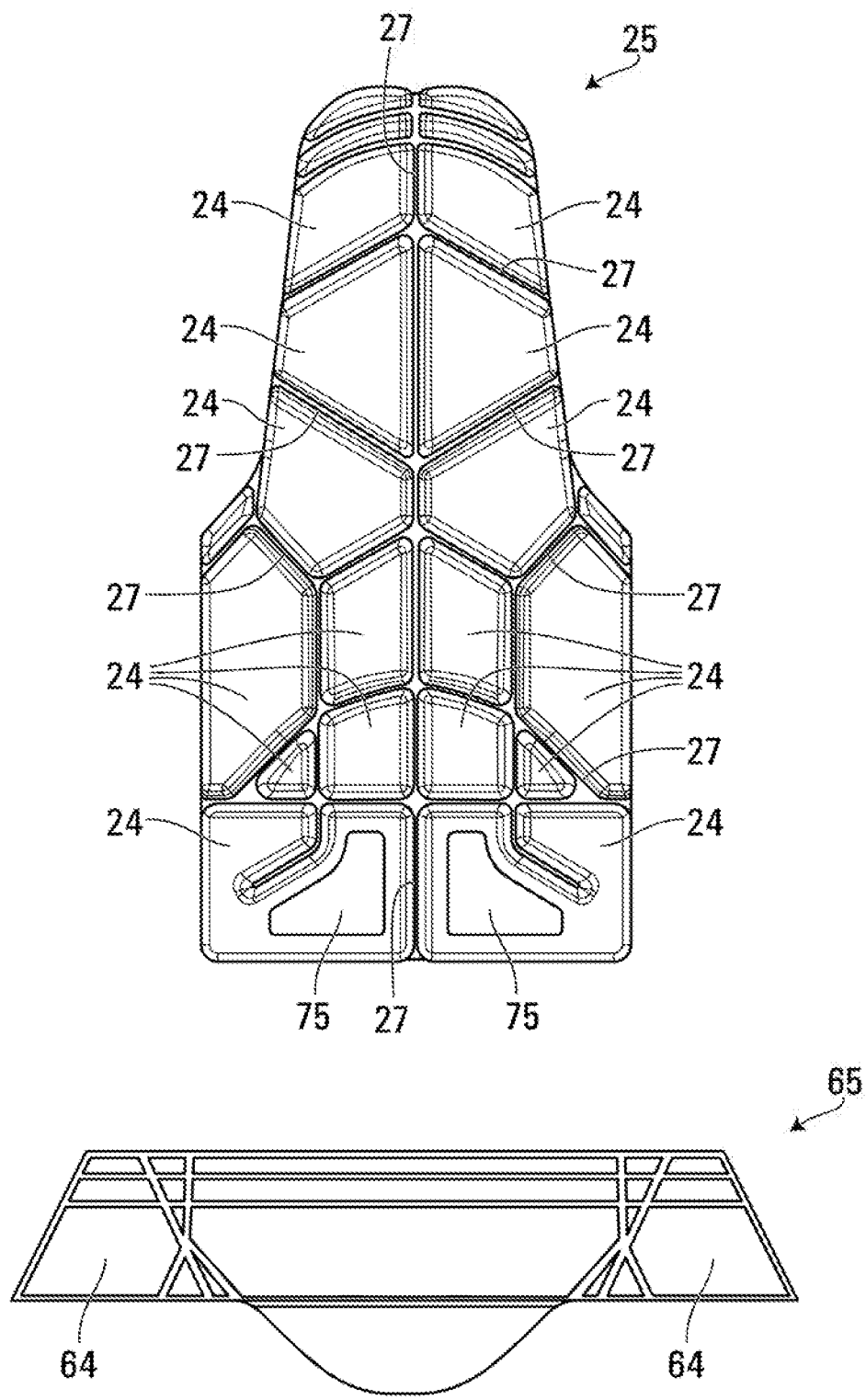
FIG. 12 is a front view of the base cushioning element and the variable cushioning element of FIG. 11.
Figure 13:
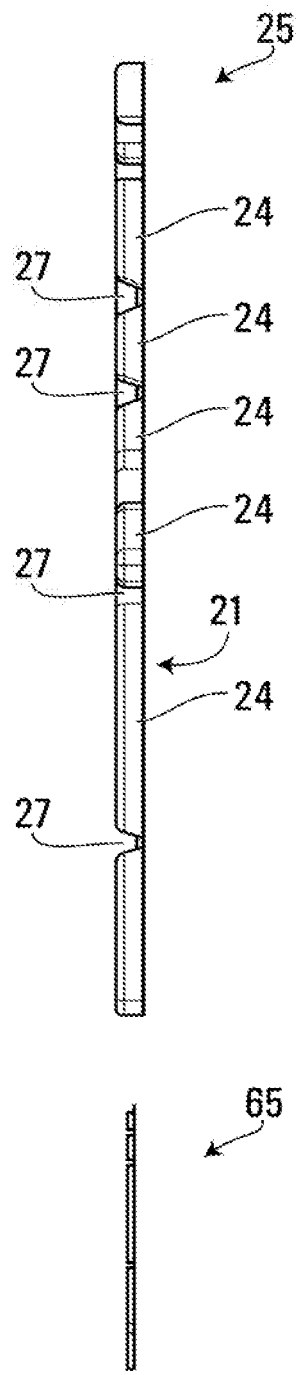
FIG. 13 is a side view of the base cushioning element and the variable cushioning element of FIG. 11.

FIGS. 9 and 10 illustrate another embodiment of a postural orthosis support apparatus 10. In this example, a modular base cushioning system includes a plurality of cushioning elements 24 extending from a securement layer 25. In this example, a single securement layer 25 covers substantially all of front face 13 of base panel 12. Alternatively, a securement layer 25 may cover a majority of front face 13. Preferably, cushioning elements 24 are separated by one or more ventilation channels 27.

Layer 25 may be secured to front face 13 of base panel 12 using an adhesive or the like. Optionally, a rear face 21 of securement layer 25 may be releasably secured to the front face 13 of base panel 12 using mechanical fasteners, such as hook and loop fasteners. For example, in the illustrated embodiment, a number of 'hook' elements 35 are secured to the front face 13 of base panel 12 (e.g. using an adhesive) and one or more 'loop' elements are provided on the rear face 21 of securement layer 25. Optionally, substantially all of the rear face 21 of securement layer 25 may be provided with 'loop' elements', which advantageously may allow for relatively small positional adjustments to be made by 'peeling' or otherwise separating securement layer 25 from 'hook' elements 35, and re-attaching the hook and loop elements with securement layer 25 in a different position relative to base panel 12.

Providing a modular base cushioning system with a number of cushioning elements extending from a common securement layer may have one or more advantages. For example, securing layer 25 to the front face 13 of base panel 12 may be simpler and/or faster than securing separate cushioning elements 24 to face 13. Additionally, or alternatively, as the spacing of cushioning elements 24 is fixed relative to securement layer 25, such a modular base cushioning system may facilitate providing a support face 20 with a relatively large number of ventilation channels 27 (and/or a relatively complex pattern of ventilation channels), e.g. as compared with securing separate cushioning elements 24 to face 13.

Figure 14:
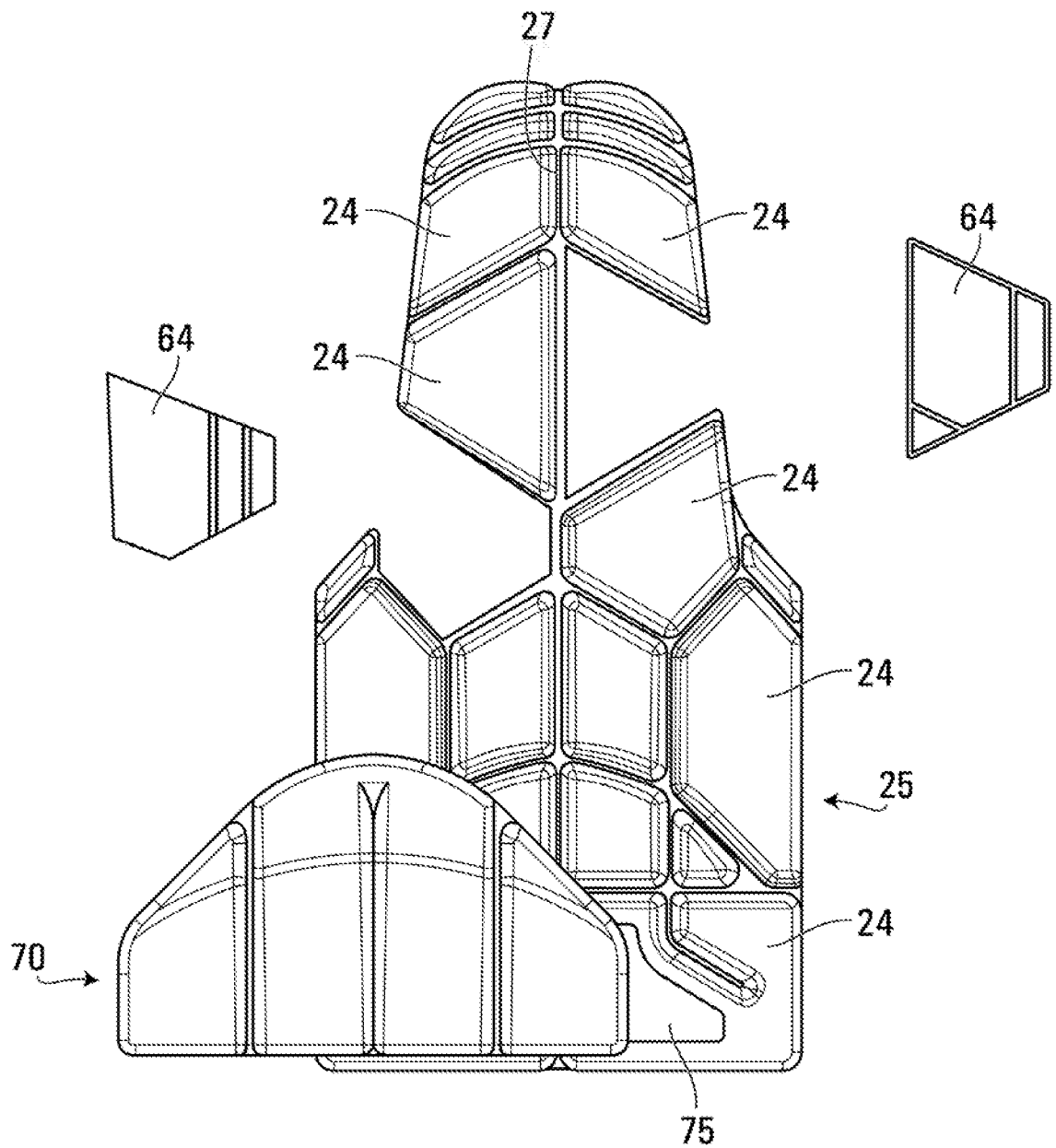
FIG. 14 is an exploded perspective view of a modified base cushioning element and a supplementary cushioning element.

Additionally, a modular base cushioning system may facilitate customization of the cushioning elements 24 that define support face 20. For example, as illustrated in FIGS. 11 to 14, a modular base cushioning system may also include one or more auxiliary cushioning elements 64 that may be used to selectively replace one or more cushioning elements 24. For example, as illustrated in FIG. 14, securement layer 25 may be cut (e.g. along one or more ventilation channels) to remove one or more cushioning elements 24, and auxiliary cushioning elements 64 that are thinner than base cushioning elements may be secured to the front face 13 of base panel 12 in place of the removed cushioning elements. Alternatively, some or all of the auxiliary cushioning elements 64 may be thicker than the base cushioning elements. Also, in some embodiments auxiliary cushioning elements 64 may have a different density than base cushioning elements 24.

In the illustrated example, auxiliary cushioning elements are provided on a securement layer 65 with ventilation channels provided between cushioning elements, similar to securement layer 25. Alternatively, or additionally, discrete auxiliary cushioning elements 64 (e.g. without ventilation channels) may be provided. Preferably, auxiliary cushioning elements may be provided in shapes that correspond with shapes of base cushioning elements, which may facilitate replacement of a base cushioning element with an auxiliary cushioning element.

Optionally, postural orthosis support apparatus 10 may include one or more supplementary cushioning elements, e.g. to provide additional cushioning at selected areas of the support face 20. In the example postural orthosis support apparatus 10 illustrated in FIGS. 9 and 10, a supplemental lumbar cushioning element 70 is provided on the front face of the lumbar portion of the base cushioning element 24. In the illustrated example, supplemental cushioning element 70 may be releasably secured using hook and loop fasteners, as 'hook' elements 75 are provided on the front face of cushioning elements 24, and one or more 'loop' elements are provided on the rear face 72 of supplemental cushioning element 70. Optionally, substantially all of the rear face 72 of supplemental cushioning element 70 may be provided with 'loop' elements', which advantageously may allow for relatively small positional adjustments to be made when securing or re-locating supplemental cushioning element 70 in a different position relative to base panel 12.

It will be appreciated that while the supplemental cushioning element 70 in the illustrated example is a provided in the lumbar portion, supplemental cushioning elements may additionally or alternatively provided in the thoracic portion.

Base panel 12 also preferably exhibits thermoplastic behavior at a relatively low softening temperature (e.g. between about 60° C. and 75° C.), so that it may be formed against a user's back (as discussed further below) without causing discomfort and/or injury. For example, FiberForm® splinting material is specified as having an optimum softening temperature of between about 66° C. and 71° C. In some embodiments, base panel 12 may be constructed from a composition that consists primarily of thermoplastic material. Advantageously, the base panel's thermoplasticity allows the panel to be heated above a softening temperature, at which point the base panel may be manipulated or otherwise deformed into a desired shape, and the panel will generally retain this shape once it has cooled below the softening temperature. A base panel that can be heated, deformed, and cooled in this manner may alternatively be characterized as a thermoformable base panel.

An advantage of the thermoplasticity of base panel 12 is that base panel 12 may be custom molded, e.g. for comfort or therapeutic reasons. For example, base panel 12 may be molded directly on the body of a user to form a customized curvature that may be: i) consistent with a preferred or optimal spinal curvature depending on the deviation of the particular user's spine; ii) intended to promote the correction of one or more specific postural dysfunctions of the particular user, and/or iii) intended to provide non-corrective support and/or comfort when worn by the particular user with a body armor carrier or other portable equipment worn on the torso.

For example, orthotic therapy for the feet may assist to maintain or restore structural and functional balance, as well as promote a discomfort-free lifestyle. The traditional method of assessing patients takes approximately one hour and requires the clinician to take a plaster or foam block mold (a static mold) of the shape of the patient's foot while the foot is static, non-weight bearing and held in its exact subtalar neutral position. In order to provide versatility and customization in the postural orthosis as disclosed herein, much like with foot orthotics, the low temperature thermoplastic base panel 12 may be shaped to functionally support or correct posture thus restoring structural and functional balance to the spine based on positioning the user or patient's spine in the neutral or optimal position while they are laying in the prone position.

Figure 7:
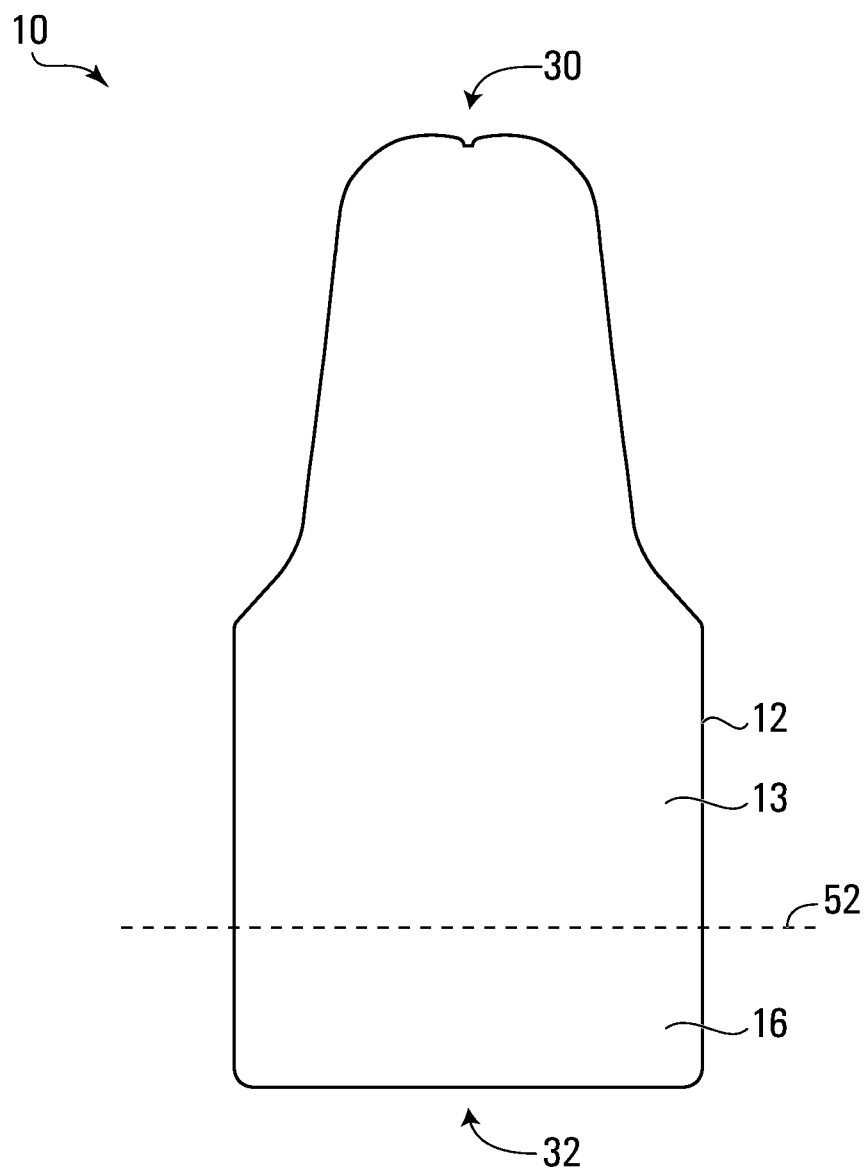
FIG. 7 is a front view of a base panel of a postural orthosis support apparatus.
Figure 8:
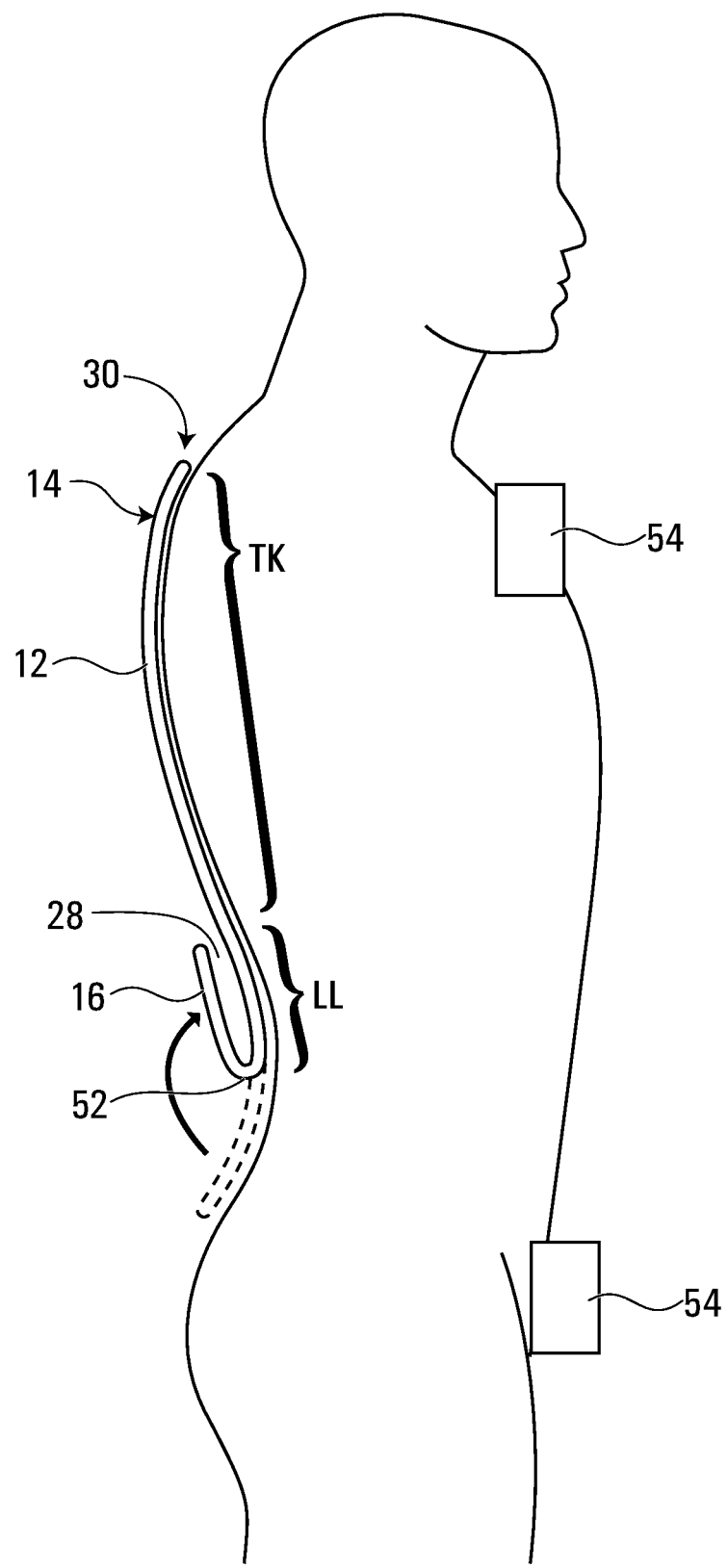
FIG. 8 is a schematic section view of the base panel of FIG. 7 being formed to a user wearing a personal body armor carrier.

For example, as illustrated in FIG. 7, a base panel 12 (e.g. a low temperature thermoplastic) of apparatus 10 may be initially provided as a flat precut shape (e.g. with no curvature) before being heated and custom molded to the body as illustrated in FIG. 8. Once heated, base panel 12 may be placed directly onto a user's back over a desired, preferred, or optimal lumbar lordosis LL and thoracic kyphosis TK (e.g. after the user's spine has been positioned in a corrective position, for example using one or more objects or posting materials 54 on the anterior of the body in the prone position as shown in FIG. 8).

Once heated base panel 12 has formed the desired curvature, it may be cooled (e.g. using active cooling—such as fans, a water jacket, or the like—or allowed to cool by ambient air) below its softening temperature to restore the base panel's resilient semi-rigidity.

In the example illustrated in FIGS. 1 to 8, engagement flange 16 is depicted as being integral to base panel 12. An integral engagement flange 16 may be formed by folding a lower portion of heated base panel 12 back on itself along a transverse fold 52 to form engagement flange 16 and channel 28. For example, with reference to FIG. 7, base panel 12 may be initially provided as a flat precut shape with no curve. Once heated, a lower portion 16 of base panel 12 may be folded transversely upon itself at a desired fold location 52 to provide the upwardly open channel 28 in which a lower edge of a ballistic panel may sit. Once folded upon itself at the desired fold location 52, base panel 12 may be custom molded to a user's body to provide a desired longitudinal curvature.

As disclosed herein, the base panel 12 and base cushioning elements 24 may form a custom molded curve to promote and/or maintain a predetermined and desired position of a user's spine. The Harrison Spinal Model and Cobb Methods are evidenced based models for sagittal (side view) spinal alignment and the study of both normal and abnormal spinal angles has established what is referred to herein as the desired position, also referred to as neutral posture or neutral spinal position. Generally, the desired position may result in a longitudinal curvature of apparatus 10 that may be convex towards the user in the thoracic spine and concave towards the user in the lumbar spine. For example, the desired position may be characterized by an average thoracic angle (T1-T12) of +43.7 degrees, with a standard deviation (SD) of ±11.4 degrees, lumbar angle (T12-S1)=−63.2 degrees (SD ±10.0 degrees), and pelvic angle=+49.4 degrees (SD ±9.9 degrees). See e.g. Keller T S, Colloca C J, Harrison D E, Harrison D D, Janik T J., Influence of spine morphology on intervertebral disc loads and stresses in asymptomatic adults: implications for the ideal spine. Spine J. 2005 May-June; 5(3):297-309).

Established techniques in the fields of ergonomics, orthopedics, physical and occupational therapies, and chiropractic may be used to determine the angles between different spinal regions or segments. For example, reference lines may be drawn and measured on radiographs of the human spine. For example, in left facing radiographs, a referencing line may be drawn across the superior edge of the T1 vertebral body and another across the inferior edge of the T12 vertebral body. These referencing lines may be extended anteriorly, or to the left, until they meet. The angle at which they meet is measured and gives rise to the thoracic spine kyphotic angle.

Similarly, to arrive at the average ideal lumbar spine angles, a referencing/measuring line may be drawn at the superior edge of the L1 vertebral body, and the inferior edge of the L5 vertebral body. The referencing lines are extended posteriorly, or to the right of the spine until they meet. This angle is measured and noted as the lumbar lordotic angle.

The Cobb Method may be used to determine optimal angles, also referred to as the Cobb angle, between different spinal regions. The Cobb angle is defined as the angle formed between a line drawn parallel to the superior endplate of one vertebra and a line drawn parallel to the inferior endplate of a vertebra below on a lateral radiograph of the spine. For example, the T1 and T12 vertebrae may be used in measuring the thoracic angle. The T12 and S1 vertebrae may be used to measure the lumbar angle. Generally, a (+) angle refers to a dorsal angle and a (−) angle refers to a ventral angle.

In some embodiments, base panel 12 may not be custom molded to a particular user. For example, the ideal lumbar lordotic and thoracic kyphotic angles may be considered neutral and may be designated as "0" which may be used to provide an 'un-molded' (e.g. non-thermoplastic) base panel 12 with a non-user specific curvature. Such a 'non-custom' postural orthosis support apparatus 10 may be intended mainly for support and comfort. Additionally, one or more different preset curves of the base panel 12 and cushioning elements 24 may be designated "+2", "+1", "−2", or "−1" depending on the degree of correction for a hyperlordosis/hypolordosis or hyperkyphosis/hypokyphosis and a 'non-custom' postural orthosis support apparatus 10 with such a designation may be primarily for therapeutic reasons, e.g. with a goal of eventually getting the user to neutral/ideal posture or "0".

Advantageously, postural orthosis support apparatus 10 may assist in distributing a load created by the weight of portable equipment being worn by the user such as: personal body armor (including soft armor and/or hard ballistic plates), backpacks, respiratory systems, and the like. For example, at least a portion of the load created by carrying portable equipment, such as body armor, may be taken up by resting on the shoulders. However, that load may change various spinal angles and cause the user to deviate from and/or prevent a user from achieving a neutral posture. For example, wearing of body armor that has an anterior weight bias may cause hyperkyphosis in the thoracic spine and hypolordosis in the lumbar spine.

When a user is carrying portable equipment, for example body armor or a backpack, the load of the equipment may be generally directed to the shoulders of the user (described as a coordinate loading in the Cartesian Coordinating system or simply as the XYZ Coordinating system as shown in FIG. 2. If the user is carrying a large and/or heavy backpack, there may be an additional load in the Z coordinate, whereby the load of the backpack will have a posterior to anterior force pressure effect. Postural orthosis support apparatus 10 may distribute this load across the spine.

Additionally, postural orthosis support apparatus 10 may provide lumbar support while the user is standing, moving, and/or when seated. This lumbar support may decrease excessive intervertebral disc loading while both standing and sitting, as well as decrease over-recruitment of the erector spinae musculature that may occur while the user is trying to carry heavy anterior loads, for example when the user is wearing body armor that is front heavy. The apparatus 10 may also help distribute loads uniformly across the back when wearing equipment, which is heavy posteriorly.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A postural orthosis support apparatus for use with a personal body armor carrier, the orthosis support apparatus comprising:
   a resilient semi-rigid base panel comprising a low temperature thermoplastic, the base panel having an upper end, a thoracic portion, a lumbar portion, a lower end, a front face, and a rear face,
   the base panel having a curvature for promoting a desired alignment of a spine of a user;
   a plurality of base cushioning elements, each cushioning element having a front face, a rear face secured to the front face of the base panel, the plurality of base cushioning elements comprising a thoracic portion and a lumbar portion; and
   at least one ventilation channel separating adjacent base cushioning elements,
   wherein the base panel is configured to be secured to the personal body armor carrier interior of a ballistic panel,
   wherein, when a user is wearing the personal body armor carrier using the postural orthosis support apparatus, a back of the user faces the front face of the base panel,
   wherein the at least one ventilation channel is defined by opposed sides of the adjacent base cushioning elements and the front face of the base panel between the adjacent base cushioning elements, and
   wherein the at least one ventilation channel has at least one open end that is open to ambient air at a terminal end of the opposed sides of the adjacent base cushioning elements, and the ventilation channel extends from a location inboard of the base panel to each open end.

2. The postural orthosis support apparatus of claim 1, wherein the base panel further comprises an engagement flange extending rearwardly and upwardly from the base panel proximate the lower end of the base panel, the engagement flange and the rear face of the base panel defining an upwardly facing channel for engaging a lower edge of the ballistic panel.

3. The postural orthosis support apparatus of claim 2, wherein the engagement flange is formed by heating the base panel above a softening temperature, folding a lower portion of the base panel back towards itself to form the engagement flange and the channel, and allowing the base panel to cool below the softening temperature.

4. The postural orthosis support apparatus of claim 3, wherein at least one interior surface of the upwardly facing channel has a textured surface for inhibiting relative movement between the base panel and the ballistic panel when the lower edge of the base panel is engaged by the upwardly facing channel.

5. The postural orthosis support apparatus of claim 2, wherein at least one interior surface of the upwardly facing channel has a textured surface for inhibiting relative movement between the base panel and the ballistic panel when the lower edge of the base panel is engaged by the upwardly facing channel.

6. The postural orthosis support apparatus of claim 1, wherein the rear face of the plurality of base cushioning elements comprises a securement layer, wherein a plurality of cushioning segments extends forwardly from the securement layer, and wherein the at least one ventilation channel is defined by sides of adjacent cushioning segments and the securement layer.

7. The postural orthosis support apparatus of claim 6, wherein one of the plurality of cushioning segments has a first thickness, and wherein another of the plurality of cushioning segments has a second thickness that is less than the first thickness.

8. The postural orthosis support apparatus of claim 6, wherein one of the plurality of cushioning segments has a first density, and wherein another of the plurality of cushioning segments has a second density that is less than the first density.

9. The postural orthosis support apparatus of claim 1, wherein the semi-rigid base panel further comprises at least one of an aramid, a para-aramid, and an ultra-high-molecular-weight polyethylene.

10. The postural orthosis support apparatus of claim 9, wherein the resilient semi-rigid base panel is customized such that the curvature is custom-formed and configured to the spine of a specific user.

11. The postural orthosis support apparatus of claim 1, wherein the resilient semi-rigid base panel is customized such that the curvature is custom-formed and configured to the spine of a specific user.

12. The postural orthosis support apparatus of claim 11, wherein the curvature is formed by heating the base panel above a softening temperature, placing the heated base panel against the specific user's back to form the curvature, and allowing the base panel to cool below the softening temperature while maintaining the curvature.

13. The postural orthosis support apparatus of claim 1, further comprising a supplementary cushioning element configured to be releasably secured to the front face of a lumbar portion of the plurality of base cushioning elements.

14. The postural orthosis support apparatus of claim 13, wherein a rear face of the supplementary cushioning element is configured to be releasably secured to the front face of the lumbar portion of the plurality of base cushioning elements by complementary hook and loop fastening elements.

15. The postural orthosis support apparatus of claim 1, wherein the rear face of the base panel is releasably secured to at least one of the ballistic panel and the personal body armor carrier by complementary hook and loop fastening elements.

16. The postural orthosis support apparatus of claim 1, wherein the rear face of the plurality of base cushioning elements are releasably secured to the front face of the base panel by complementary hook and loop fastening elements.

17. The postural orthosis support apparatus of claim 1, wherein at least a portion of the front face of the base panel is exposed when the plurality of base cushioning elements are secured to the front face of the base panel, the exposed portion including the at least one ventilation channel.

18. The postural orthosis support apparatus of claim 1, wherein one of the plurality of base cushioning elements has a first thickness, and wherein another of the plurality of base cushioning elements has a second thickness that is less than the first thickness.

19. The postural orthosis support apparatus of claim 1, wherein one of the plurality of base cushioning elements has a first density, and wherein another of the plurality of base cushioning elements has a second density that is less than the first density.

\* \* \* \* \*